United States Patent [19]

Ondetti et al.

[11] Patent Number: 4,684,660

[45] Date of Patent: Aug. 4, 1987

[54] MERCAPTOACYLDEPEPTIDES

[75] Inventors: Miquel A. Ondetti, Princeton; Josip Pluscec, Ewing Twp., Mercer County, both of N.J.

[73] Assignee: E. R. Squibb & Sons, Inc., Princeton, N.J.

[21] Appl. No.: 145,516

[22] Filed: May 1, 1980

Related U.S. Application Data

[63] Continuation of Ser. No. 25,701, Apr. 2, 1979, abandoned.

[51] Int. Cl.$^4$ ............... A61K 31/40; A61K 31/405; A61K 31/425; A61K 37/43; C07D 207/00; C07D 275/02
[52] U.S. Cl. .................... 514/423; 514/419; 514/564; 548/530; 548/532; 548/533; 548/214
[58] Field of Search ............... 424/177; 514/423, 419, 514/564; 548/530, 532, 533, 214

[56] References Cited

U.S. PATENT DOCUMENTS

| | | | |
|---|---|---|---|
| 3,246,025 | 4/1966 | Mita et al. | 424/177 |
| 3,897,480 | 7/1975 | Mita et al. | 424/177 |
| 4,248,883 | 2/1981 | Sawajama et al. | 424/274 |

OTHER PUBLICATIONS

Y. Suguira, Inorganic Chemistry, vol. 17, No. 8, pp. 2176–2182, (1978).
Sugiura, et al., Bioinorganic Chemistry, vol. 9, pp. 521–528 (1978).
Ariens, Drug Design vol. 11, (1971) 57 and 58 and 337–338.
Parsons, Peptide Hormones 1–7.
Boyer; The Enzymes vol. III 1971, pp. 6 and 7.
Biological Abstr. 65, p. 60613.
Biological Abstr. 63, p. 25801.
Biological Abst. 66, p. 4592.
Biological Abstr. 65, p. 66598.
Biological Abstr. 65, p. 28660.

*Primary Examiner*—Delbert R. Phillips
*Attorney, Agent, or Firm*—Lawrence S. Levinson; Donald J. Barrack

[57] ABSTRACT

Compounds having the formula

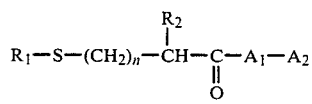

and alkyl esters and salts thereof.
$R_1$ is hydrogen, alkanoyl or

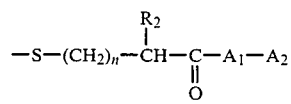

$R_2$ is hydrogen, alkyl, or phenylalkyl;
n is 0 or 1; and
$A_1$ and $A_2$ each is an α-amino or α-imino acid residue joined through a peptide bond, have useful hypotensive activity.

22 Claims, No Drawings

MERCAPTOACYLDEPEPTIDES

This application is a continuation of copending U.S. patent application Ser. No. 25,701, filed Apr. 2, 1979, and now abandoned.

BACKGROUND OF THE INVENTION

U.S. Pat. No. 4,105,776 issued Aug. 8, 1978 describes a group of thioalkanoyl derivatives of azetidine-, pyrrolidine-and piperidinecarboxylic acid compounds having the structural formula

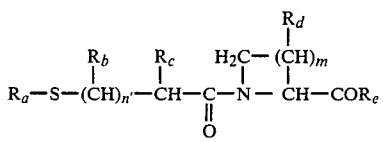

wherein the symbols can be, inter alia, as follows: $R_a$ can be hydrogen, lower alkyl, phenyl, substituted phenyl, phenyl-lower alkyl,

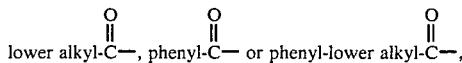

$R_b$ can be hydrogen, $R_c$ can be hydrogen or lower alkyl, $R_d$ can be hydrogen, hydroxy or lower alkyl, $R_e$ can be hydroxy, $-NH_2$ or lower alkoxy, $n'$ can be 0,1 or 2 and m can be 1, 2 or 3. The compounds, and the salts thereof, are disclosed as being useful as inhibitors of the conversion of the decapeptide angiotensin I to angiotensin II, and are, therefore, useful in reducing or relieving angiotensin related hypertension. Among the salts disclosed are amino acid salts.

U.S. Pat. No. 3,246,025, issued Apr. 12, 1966 α-and β-mercaptopropionylglycine and esters and amides thereof. The compounds are disclosed as being useful for the treatment of drug intoxication and poisoning and for strengthening liver function.

U.S. Pat. No. 3,897,480 issued July 29, 1975 discloses N-(mercaptoacyl)amino acids having the formula

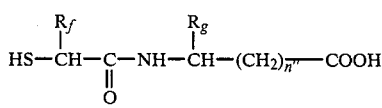

wherein the symbols can be as follows: $R_f$ can be alkyl, aryl or arylalkyl, $R_g$ can be hydrogen, alkyl, aryl or arylalkyl and $n''$ can be 0, 1, 2, 3 or 4 with various provisos that further limit the disclosure. The compounds are disclosed as having an accelerating action for the elimination of a heavy metal such as mercury from the body, an eliminating action with respect to a substance harmful to the body such as a free radical or a peroxide; and an accelerating action of metabolism.

BRIEF DESCRIPTION OF THE INVENTION

Compounds having the formula

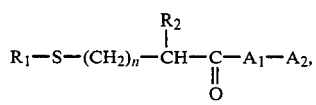

and alkyl esters and salts thereof, have useful hypotensive activity. In formula I, and throughout the specification, the symbols are as defined below.

$R_1$ is hydrogen, alkanoyl or

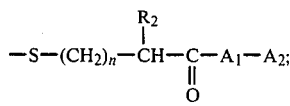

$R_2$ is hydrogen, alkyl, or phenylalkyl;
n is 0 or 1; and
$A_1$ and $A_2$ each is an α-amino or α-imino acid residue joined through a peptide bond.

The term "alkyl", as used throughout the specification, refers to groups having 1 to 7 carbon atoms.

The term "alkanoyl", as used throughout the specification, refers to alkanoyl groups having 2 to 7 carbon atoms. Acetyl is the preferred alkanoyl group.

The α-amino and α-imino acid residues represented by $A_1$ and $A_2$ can be either naturally occurring or synthetic. Exemplary groups are proline, 4-hydroxyproline, 4,4-ethylenedioxyproline, 4-methoxyproline, 4-thiazolidinecarboxylic acid, tryptophane, glycine, alanine, leucine, isoleucine and valine. As set forth above, the $A_1$ and $A_2$ groups are linked by "a peptide bond"; i.e., the linkage

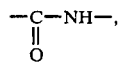

between the α-carboxyl group of the residue $A_1$ and the α-amino or α-imino group of the group $A_2$.

DETAILED DESCRIPTION OF THE INVENTION

Specifically contemplated as part of this invention are all of the mercaptoacyldipeptides of formula I. Those compounds of formula I wherein n is O are preferred. Also preferred are those compounds of formula I wherein the α-amino or α-imino residues of $A_1$ and $A_2$ are in the L-configuration. Compounds of formula I wherein $A_1$ is α-amino and $A_2$ is α-imino (especially L-proline) also constitute a preferred group.

The mercaptoacyldipeptides of formula I wherein $R_1$ is alkanoyl can be prepared by acylation of a dipeptide having the formula $$A_1-A_2, \qquad \qquad II$$

or an alkyl ester derivative thereof, with a thio acid having the formula

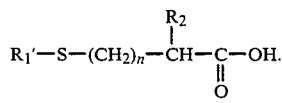

In formula III, and throughout the specification, the symbol $R_1'$ is alkanoyl. The above acylation can be accomplished using any one of the numerous techniques well known in the art. For example, the acylation can be affected in the presence of a coupling agent such as a carbodiimide (of which dicylohexylcarbodiimide is the most often used). Alternatively, the thio acid of formula III can be activated by formation of its mixed anhydride, symmetrical anhydride, acid chloride or active ester, or by the use of Woodward reagent K or N-ethoxycarbonyl-2-ethoxy-1,2-dihydroquinoline. For a more detailed discussion of various acylation techniques, reference is made to Methoden der organischen Chemie (Houben-Weyl), Vol. XV, part II, page 1 et seq. (1974).

An alternative synthesis for the compounds of formula I wherein $R_1$ is alkanoyl comprises the acylation of the amino acid "$A_1$", with a mercaptoalkanoyl acid of formula III (using the procedure described above) to obtain a mercaptoalkanoyl amino acid having the formula

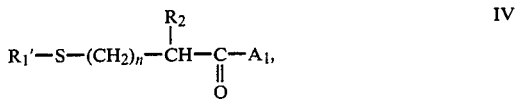

followed by acylation of the amino acid "$A_2$" or alkyl ester thereof, with a mercaptoalkanoyl amino acid of formula IV. The acylation can be accomplished using any one of the well known techniques for coupling amino acids. For a review of these techniques reference should be made to Bodanszky and Ondetti, *Peptide Synthesis*, Interscience Publishers (1966).

Compounds of formula I wherein $R_1$ is hydrogen can be prepared by ammonolysis or alkaline hydrolysis of the corresponding compounds of formula I wherein $R_1$ is alkanoyl, which can be obtained utilizing either of the procedures described above. Compounds of formula I wherein $R_1$ is

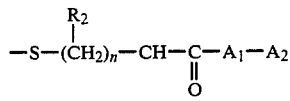

can be prepared by oxidation of the corresponding free thiol of formula I.

Alternatives to the above syntheses will be apparent to the practitioner of this invention. For example, if an ester of $A_1$—$A_2$ or $A_2$ is used in one of the above syntheses, the corresponding free acid can be obtained from the esterified product by acid or alkaline hydrolysis.

Mercaptoalkanoyl acids of formula III and mercaptoalkanoyl amino acids of formula IV, and methods for their preparation, are described in the literature; see, for example, U.S. Pat. Nos. 4,046,889, 4,105,776 and 4,053,651.

The compounds of this invention form basic salts with various inorganic and organic bases which are also within the scope of the invention. Such salts include ammonium salts, alkali metal salts like sodium and potassium salts (which are preferred), alkaline earth metal salts. like the calcium and magnesium salts, salts with organic bases e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The compounds of formula I, and the alkyl esters and salts thereof, are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of compounds of formula I, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 50 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are specific embodiments of this invention.

EXAMPLE 1

1-[N-(Acetylthioacetyl)glycyl]-L-proline

Glycyl-L-proline (1.72 g) is taken into 10 ml of 1N sodium hydroxide with stirring in an ice bath. To this 5 ml of 2N sodium hydroxide is added followed by 1.13 g of chloracetyl chloride and the bath is removed. After three hours at room temperature, thiolacetic acid (836 mg) and potassium carbonate (960 mg) in 10 ml of water is added and the reaction is stirred for about 16 hours at room temperature. The reaction is acidified with sulfonated polystyrene cation exchange resin, eluted with water and concentrated to dryness in vauco. This was taken into acetic acid and the insolubles (melting point over 320° C.) are filtered. The filtrate is concentrated to dryness in vacuo and 7:3 chloroform acetic acid is added. The product is centrifuged and the supernate applied to a 60 g silica gel column and eluted with 7:3 chloroform: acetic acid yielding 1.0 g of the title compound.

EXAMPLE 2

1-[N-(Mercaptoacetyl)glycyl]-L-proline

1-[N-(Acetylthioacetyl)glycyl]-L-proline (1.0 g) is treated for thirty minutes under argon in a solution of 6 ml water and 6 ml concentrated sodium hydroxide. The solution is concentrated in vacuo, acidified with sulfonated polystyrene cation exchange resin, applied to a column of the same and eluted with water. The 800 mg of material yielded therein (plus 200 mg from a previous preparation) is chromatographed on a 30 g column of silica gel with 7:3 chloroform: acetic acid. This product (740 mg) is applied to an 85 ml column of diethylaminoethyl dextran anion exchange resin and eluted with a linear gradient of 0.005 M ammonium bicarbonate to 0.5 M ammonium bicarbonate (750 ml each). The product is converted to the free acid on sulfonated polystyrene cation exchange resin, and then treated with 7 ml of acetic acid and 350 ml of zinc dust with stirring under an argon blanket for six hours. The suspension is centrifuged, and the supernate concentrated to dryness in vacuo, taken into water and lyophilized. This is acidified with sulfonated polystyrene resin, applied to a column of the same and eluted with water yielding 365 mg of the title compound.

EXAMPLE 3 t-Butyl ester of (S)-1-[3-(acetylthio)-2-methyl 1-oxopropyl]-L-prolyl-L-proline

To a solution of 7.8 g of 1-[S-3-(acetylthio)-2-methyl-1-oxopropyl]-L-proline in 75 ml of dichloromethane is added 5.13 g of t-butyl-L-prolinate, and the solution is cooled to 5° C. To this solution is added (dropwise) a solution of dicyclohexylcarbodiimide in 50 ml of dichloromethane. The reaction is carried out at room temperature for about 16 hours. After the precipitate is removed, the resulting solution is successively washed with water, 5% sodium bicarbonate, water, 10% potassium bisulfate, and water, and then dried over sodium sulfate. The crude product (12 g) that is obtained after the solvent is removed, solidifies on standing. Recrystallization from ethyl acetate: pentane yields the title compound, melting point 104°-106° C.

EXAMPLE 4

1-(S-3-mercapto-2-methyl-1-oxopropyl)-L-prolyl-L-proline t-Butyl ester of 1-[S-3-(acetylthio)-2-methyl-1-oxopropyl]-L-proline (12 g) is taken into 60 ml of redistilled trifluoroacetic acid and the resulting solution is allowed to stand at room temperature for 1 hour. Trifluoroacetic acid is removed in vacuo and the residue is carefully dried in high vacuo for 24 hours. The heavy oil is dissolved in 30 ml of methanol and to this is added 20 ml of concentrated ammonium hydroxide. The mixture is kept at room temperature for 1 hour, and the solvent is then removed in vacuo and the oil residue is dried and treated with 6 ml of dicyclohexylamine. The salt is treated with ether and an oil precipitates The oil is taken into ethyl acetate and the solution is washed with 10% potassium bisulfate and then dried over sodium sulfate. After removal of the solvent, the residue is taken into methanol and the entire amount is adsorbed on silica gel. The solvent is removed and the silica gel containing the adsorbed product is applied to a silica gel column made up in chloroform. The column is eluted with chloroform and the mercapto positive fractions are combined. The solvent is removed and the residue is lyophilized from water to yield 1.05 g of the title compound.

EXAMPLE 5

N-(Acetylthioacetyl)-L-valyl-L-proline

A solution of t-butyloxycarbonyl-L-valyl-L-proline (3.1 g) in trifluoracetic acid (20 ml) is kept at room temperature for 15 minutes, the solvent removed in vacuo and the oily residue is dried in vacuo for several hours. The oil is taken into dimethylformamide (25 ml) and to this solution N-hydroxysuccinimide ester of acetylmercapto acetic acid (2.2 g) is added. The reaction is carried out at pH 7.5 (adjusted with triethylamine) and at room temperature for 17 hours. After removal of the solvent, the residue is taken into ethyl acetate and the solution is washed successively with water, 10% potassium bisulfate, water, saturated sodium bicarbonate, water and finally dried over sodium sulfate, yielding 4.8 g of the title compound as an oil.

EXAMPLE 6

N-(Mercaptoacetyl)-L-valyl-L-proline

N-(Acetylthioacetyl)-L-valyl-L-proline (4.8 g) is taken into a mixture of 12 ml of methanol and 7.5 ml of concentrated ammonium hydroxide and the resulting solution is kept at room temperature for 1 hour. The pH is adjusted to 7 and methanol is removed in vacuo. The remaining aqueous layer is acidified to pH 2 with 2N hydrochloric acid and the solution is saturated with sodium chloride. The product is extracted with ethyl acetate, the solution is dried over sodium sulfate and the solvent is removed in vacuo, yielding 2 g of material, melting point 158°-162° C. Recrystallization from ethyl acetate (with the addition of a small amount of methanol) yields the product, melting point 162°-165° C. After drying a sample at 55° C. for 2 hours the melting point is 190°-192° C.

EXAMPLE 7

1-[(S-3-(Acetylthio)-2-methyl-1-oxopropyl]-L-prolylglycine, ethyl ester

Following the procedure of Example 3, but utilizing 10.4 g of 1-[S-3-(acetylthio)-2-methyl-1-oxopropyl]-L-proline, 100 ml of dichloromethane, 5.6 g of the ethyl ester of glycine (prepared from 5.58 g of the hydrochloride salt of the ethyl ester of glycine and 5.6 ml of triethylamine in 50 ml of dichloromethane) and 8.24 g of dicyclohexylcarbodiimide, yields 11.2 g of the title compound as a viscous oil.

EXAMPLE 8

(S)-1-(3-Mercapto-2-methyl-1-oxopropyl)-L-prolylglycine, lithium salt

1-[S-3-(Acetylthio)-2-methyl-1-oxopropyl]-L-prolylglycine, ethyl ester (11.2 g) is taken into methanol (200 ml) to which an aqueous solution of potassium hydroxide (9 g in 40 ml of water) is added. The hydrolysis is allowed to proceed at room temperature for two hours. The organic solvent is removed in vacuo and the aqueous residue is adjusted to pH 7.0. The product is extracted with ethyl acetate, the solution dried over sodium sulfate and the solvent is removed in vacuo. The residue (3.5 g) is taken into water and the pH is adjusted to pH 2.0. The free acid is again taken into ethyl acetate using sodium chloride to decrease the solubility in water. The residue after removal of the solvent, is lyophilized from water, yielding 2.16 g of the free base of the title compound. The entire amount was taken into water and the pH carefully adjusted to pH 7.0 using 0.05N lithium hydroxide. The solution is lyophilized to yield 1050 mg of the title compound.

EXAMPLE 9

(S)-1-(3-Mercapto-2-methyl-1-oxopropyl)-L-prolyl-L-alanine

Following the procedure of Examples 3 and 4, but utilizing 7.8 g of 1-[S-3-(acetylthio)-2-methyl-1-oxopropyl]-L-proline, 75 ml of dimethyl-formamide, 6.2 g of dicyclohexylcarbodiimide, 4.2 g of the hydrochloride salt of the methyl ester of L-alanine and 4.2 ml of triethylamine (pH 7.5–8.0), yields 8 g of material. This material is passed through a silica gel column using ethyl acetate as an eluant. Two fractions are obtained ($R_f$=0.76 and $R_f$=0.4, silica gel, ethyl acetate).

The slower moving fraction (2 g $R_f$=0.4) is taken into potassium hydroxide/aqueous methanol (1.5 g potassium hydroxide in 7 ml of water and 35 ml of methanol) and the solution is kept at room temperature for 2 hours. The organic solvent is removed in vacuo and the aqueous layer is acidified to pH 2.0. After the addition of sodium chloride, the product is extracted five times with ethyl acetate. The solution is dried and the solvent is removed in vacuo. The solid residue is crystallized from hot ethyl acetate, yielding 1 g of product, melting point 128°–130° C.

EXAMPLE 10

Acetylthioacetyl-valyl-tryptophan methyl ester

A solution of 15 g of the methyl ester of t-butyloxycarbonyl-valyl-tryptophan in 150 ml of trifluoracetic acid and 15 ml of anisole is stirred for 1 hour under nitrogen. The solution is stripped in vacuo to an oily residue.

A solution of 4.83 g of acetylthioacetic acid and 6.18 g of hydroxybenzotriazole monohydrate in 120 ml of tetrahydrofuran is cooled to 0° C. and treated with a solution of 8.16 g of dicyclohexylcarbodiimide in 60 ml of tetrohydrofuran. The mixture is stirred at 0° C. for 0.5 hour and then at room temperature for 1 hour. The precipitated urea is filtered and the filtrate is stripped in vacuo to a white solid. The active ester is dissolved in 90 ml of dimethylformamide after which a solution of the above dipeptide methyl ester trifluoroacetic acid salt in 60 ml of dimethylformamide is added along with sufficient N-methyl morpholine to maintain the pH at 7.5 and the resultant mixture is stirred for 16 hours at room temperature. The reaction mixture is stripped in vacuo to an oil which is partitioned between ethyl acetate and water. The ethyl acetate phase is washed with 2N citric acid, water, saturated sodium bicarbonate solution, and water, and dried over sodium sulfate and stripped to a solid. The material is crystallized from ethyl acetate: pentane to yield 10 g of the title compound, melting point 110°–112° C.

EXAMPLE 11

N-(Mercaptoacetyl)-L-valyl-L-tryptophan, lithium salt

Acetylthioacetyl-valyl-tryptophan methyl ester (5.0 g) is dissolved in 52 ml of methanol and a solution of 2.1 g of potassium hydroxide in 10.5 ml of water is added. The mixture is stirred under nitrogen at room temperature for 1.5 hours after which the methanol is stripped in vacuo. The aqueous remainder is diluted with water, extracted with ethyl acetate and acidified to pH 2.0 with 6N hydrochloric acid. The solid is filtered, washed with water and dried yielding 3.4 g of material. The solid is chromatographed on a Sephadex LH-20 column using 7:3 methanol: water as eluant to yield 1.5 g of an oil. The oil is dissolved in 1:1 ethanol: water and adjusted to pH 7.0 with 0.1N lithium hydroxide. A small amount of insoluble material is removed by filtration and the filtrate is stripped in vacuo to an oil. The oil is dissolved in water and lyophilized to yield 1.5 g of a solid.

EXAMPLE 12

(S)-1-3-(Acetylthio)-2-methyl-1-oxopropyl]-L-prolyl-D-alanine methyl ester

To a solution of 1-[S-3-(acetylthio)-2-methyl-1-oxopropyl]-L-proline (7.8 g) in acetonitrile (150 ml) carbonyldiimidazole (4.9 g) is added at 0° C. The mixture is stirred for 1 hour at this temperature after which the solution becomes almost clear and D-alanine methyl ester hydrochloride (4.2 g) is added. The pH-value is adjusted to 7.5–8.0 with triethylamine (4.2 ml) and the reaction mixture is stirred for 17 hours at room temperature. The precipitate and the solvent are removed and the oily residue is taken into ethyl acetate. The solution is successively washed with water, 0.1N HCl, water, saturated NaHCO$_3$, water and dried. After removal of the solvent the remaining oil shows one spot on tlc (silica gel, EtOAc and CHCl3:MeOH 9:1) at $R_f$=0.5 with a trace at $R_f$=0.75 (in ethyl acetate). Yield: 4 g.

EXAMPLE 13

(S)-1-(3-Mercapto-2-methyl-1-oxopropyl)-L-prolyl-D-alanine (S)-[3-(Acetylthio)-2-methyl 1-oxopropyl]-L-prolyl-D-alanine methyl ester (4 g) is taken into potassium hydroxide/aqueous methanol (3 g of potassium hydroxide in 14 ml of water and 70 ml of methanol) and the solution is kept at room temperature for 2 hours. The product (2.1 g) is isolated using the procedure described in Example 9.

EXAMPLE 14

1-[N-(Mercaptoacetyl)-L-alanyl]-L-proline

To a solution of acetylthioacetic acid (1.3 g) and hydroxybenzotriazole (1.44 g) in tetrahydrofuran (39 ml), dicyclohexyl carbodiimide (2 g) is added and the mixture is stirred at 0° C. for thirty minutes and at room temperature for one hour. The precipitate is removed by filtration, and to the filtrate is added L-alanyl-L-proline as its trifluoracetate salt (prepared from t-butyloxycarbonyl-L-alanyl-L-proline, 2.8 g, and trifluoroacetic acid). The pH is adjusted to 7.5–8.0 with N-methylmorpholine and the reaction is allowed to proceed at room temperature for about 16 hours. The solvents are removed in vacuo and the residue is dissolved in a mixture of methanol (18 ml) and concentrated ammonium hydroxide (18 ml). After thirty minutes the mixture is concentrated in vacuo, the residue is dissolved in water and applied to a column of sulfonated polystyrene cation exchange resin eluting with water. This material is further purified by silica gel chromatography (acetic acid:chloroform,7:3) and crystallized from ethyl acetate, 850 mg, melting point 152°–155° C.[$\alpha$]$_D$= −128° (c=1.5, 50% aqueous MeOH).

EXAMPLE 15

1-[N-(Mercaptoacetyl)-L-alanyl]-L-thiazolidine-4-carboxylic acid

Following the procedure of Example 14, but substituting the trifluoroacetic acid salt of L-alanyl-L-thiazolidine-4-carboxylic acid for the trifluoroacetic acid salt of L-alanyl-L-proline in the procedure of Example 14, yields the title compound.

EXAMPLE 16

1-[N-(Mercaptoacetyl)-L-alanyl]-4-methoxy-L-proline

Following the procedure of Example 14, but substituting the trifluoroacetic acid salt of L-alanyl-4-methoxy-L-proline for the trifluoroacetic acid salt of L-alanyl-L-proline, yields the title compound.

EXAMPLE 17

1-[N-(Mercaptoacetyl-L-alanyl]-4-hydroxy-L-proline

Following the procedure of Example 14, but substituting the trifluoracetic acid salt of L-alanyl-4-hydroxy-L-proline for the trifluoroacetic acid salt of L-alanyl-L-proline, yields the title compound.

EXAMPLE 18

1-[N-(Mercaptocetyl)-L-alanyl]-4,4-ethylenedioxy-L-proline ethylenedioxy-L-proline Following the procedure of Example 14, but substituting L-alanyl-4,4-ethylenedioxy-L-proline for the trifluoroacetic acid salt of L-alanyl-L-proline, yields the title compound.

EXAMPLE 19

1-[N-(2-Mercaptopropanoyl)-L-alanyl]-L-proline

Following the procedure of Example 14, but substituting 2-acetylthiopropionic acid for the 2-acetylthioacetic acid, yields the title compound.

EXAMPLE 20

1-[N-(2-Mercapto-3-phenylpropanpyl)-L-alanyl]-L-proline

Following the procedure of Example 14, but substituting 2-acetylthio-3-phenylpropionic acid for 2-acetylthioacetic acid, yields the title compound.

EXAMPLE 21

1-[N-(2-Mercaptopropanoyl)-L-alanyl]-4-hydroxy-L-proline

Following the procedure of Example 14, but substituting 2-acetylthiopropionic acid for acetylthioacetic acid and the trifluoroacetic acid salt of L-alanyl-4-hydroxy-L-proline for the trifluoroacetic acid salt of L-alanyl-L-proline, yields the title compound.

EXAMPLE 22

1-[N-(2-Mercaptopropanoyl)-L-alanyl]-L-thiazolidine-4-carboxylic acid

Following the procedure of Example 14, but substituting 2-acetylthiopropionic acid for acetylthioacetic acid and the trifluoroacetic acid salt of L-alanyl-L-thiazolidine-4-carboxylic acid salt for the trifluoroacetic acid salt of L-alanyl-L-proline, yields the title compound.

EXAMPLE 23

1-[N-(2-Mercaptopropanoyl)-L-alanyl]-4-methoxy-L-proline

Following the procedure of Example 14, but substituting 2-acetylthiopropionic acid for acetylthioacetic acid and the trifluoroacetic acid salt of L-alanyl-4-methoxy-L-proline for the trifluoroacetic acid salt of L-alanyl-L-proline, yields the title compound.

EXAMPLE 24

1-[N-(2-Mercaptopropanoyl)-L-alanyl]-4,4-ethylenedioxy-L-proline

Following the procedure of Example 14, but substituting 2-acetylthiopropionic acid for acetylthioacetic acid and L-alanyl-4,4-ethylenedioxy-L-proline for the trifluoroacetic acid salt of L-alanyl-L-proline, yields the title compound.

EXAMPLE 25

1-[N-(2-Mercapto-3-phenylpropanoyl)-L-alanyl]-4-hydroxy-L-proline

Following the procedure of Example 14, but substituting 2-acetylthio-3-phenylpropionic acid for acetylthioacetic acid and the trifluoroacetic acid salt of L-alanyl-4-hydroxy-L-proline for the trifluoroacetic acid salt of L-alanyl-L-proline, yields the title compound.

EXAMPLE 26

1-[N-(2-Mercapto-3-phenylpropanoyl)-L-alanyl]-L-thiazolidine-4-carboxylic acid

Following the procedure of Example 14, but substituting 2-acetylthio-3-phenylpropionic acid for acetylthioacetic acid and the trifluoroacetic acid salt of L-alanyl-L-thiazolidine-4carboxylic acid for the trifluoroacetic acid salt of L-alanyl-L-proline yields the title compound.

EXAMPLE 27

1-[N-(2-Mercapto-3-phenylpropanoyl)-L-alanyl]-4-methoxy-L-proline

Following the procedure of Example 14, but substituting 2-acetylthio-3-phenylpropionic acid for acetylthioacetic acid and the trifluoroacetic acid salt of L-alanyl-4-methoxy-L-proline for the trifluoroacetic acid salt of L-alanyl-L-proline, yields the title compound.

EXAMPLE 28

1-[N-(2-Mercapto-3-propanoyl)-L-alanyl]-4,4-ethylenedioxy-L-proline

Following the procedure of Example 14, but substituting 2-acetylthio-3-phenylpropionic acid for acetylthioacetic acid and L-alanyl-4,4-ethylenedioxy-L-proline for the trifluoroacetic acid salt of L-alanyl-L-proline, yields, the title compound.

EXAMPLE 29

1-[N-(Mercaptoacetyl)-L-proline]-L-proline

Method A

Benzyloxycarbonyl-L-prolyl-L-proline (3 g) is hydrogentated in a mixture of absolute ethanol (50 ml) and N-hydrochloric acid (7.5 ml) in the presence of 10% palladium on charcoal. After five hours the catalyst is filtered off and the solvent is removed in vacuo. The residue is dissolved in a mixture of dimethylformamide (15 ml) and triethylamine (1.05 ml) and acetylthioacetic acid N-hydroxysuccinimido ester (1.7 g) is added. After storage at room temperature for about 16 hours the solvents are removed in vacuo and the residue is chromatographed on a column of silica gel (benzene:hexane, 7:1). This material is dissolved in trifluoroacetic acid (5 ml) and anisole (2 ml) and the solution is kept at room temperature for one hour. The reaction mixture is concentrated to dryness, and the residue is dissolved in 7.7 ml of N sodium hydroxide with stirring under argon. After fifteen minutes the mixture is neutralized with sulfonated polystyrene cation exchange resin, applied to a column of the same resin and eluted with water. The material obtained is crystallized from ethyl acetate and has a melting point 182°-183° C.

Method B

Dicyclohexylcarbodiimide (2.06 g) and 1-(acetylthioacetyl) L-proline (2.3 g) are added to a solution of L-proline t-butyl ester (1.7 g) and hydroxybenzotriazole (1.5 g) in dichloromethane (15 ml) chilled in an ice bath. After stirring at 5° C. for about 16 hours, the resulting precipitate is filtered off and the filtrate is washed until neutral. The organic layer is concentrated to dryness and the residue is purified by silica gel chromatography and crystallized from ether-hexane, yielding material with a melting point 95°-98° C. This material is deprotected by sequential treatment with trifluoroacetic acid and sodium hydroxide as described in Method A.

What is claimed is:

1. A compound having the formula

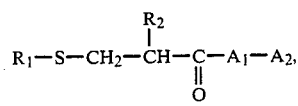

or an alkyl ester or a salt thereof, wherein
$R_1$ is hydrogen, or

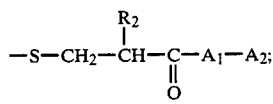

$R_2$ is hydrogen, alkyl or phenylalkyl; and
$A_1$ and $A_2$ each is an α-amino or α-imino acid residue joined through a peptide bond.

2. A compound in accordance with claim 1 wherein $R_1$ is hydrogen.

3. A compound in accordance with claim 1 wherein $R_1$ is

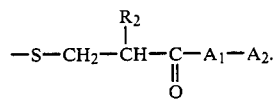

4. A compound in accordance with claim 1 wherein $R_2$ is hydrogen.

5. A compound in accordance with claim 1 wherein $R_2$ is alkyl.

6. A compound in accordance with claim 1 wherein $R_2$ is phenylalkyl.

7. A compound in accordance with claim 1 wherein $A_1$ is an α-amino acid residue and $A_2$ is an α-imino acid residue.

8. A compound in accordance with claim 7 wherein $A_2$ is L-proline.

9. A compound having the formula

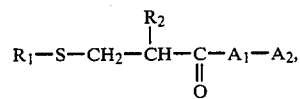

or an alkyl ester or a salt thereof, wherein
$R_1$ is hydrogen, or

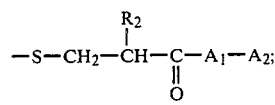

or an alkyl ester or a salt thereof, wherein
$R_2$ is hydrogen, alkyl or phenylalkyl; and
$A_1$ and $A_2$ each is independently proline, 4-hydroxyproline, 4,4-ethylenedioxyproline, 4-methoxyproline, 4-thiazolidinecarboxylic acid, tryptophane, glycine, alanine, leucine, isoleucine or valine.

10. The compound in accordance with claim 9, 1-(S-3-mercapto-2-methyl-1-oxopropyl)-L-prolyl-L-proline.

11. The compound in accordance with claim 9, 1-(S-3-mercapto-2-methyl-1-oxopropyl)-L-prolyl-glycine, lithium salt.

12. The compound in accordance with claim 9, (S)-1-(3-mercapto-2-methyl-1-oxopropyl)-L-prolyl-L-alanine.

13. The compound in accordance with claim 9, (S)-(3-mercapto-2-methyl-1-oxopropyl)-L-propyl-D-alanine.

14. A compound in accordance with claim 9 wherein $R_1$ is hydrogen.

15. A compound in accordance with claim 9 wherein $R_1$ is

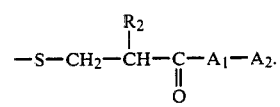

16. A compound in accordance with claim 9 wherein $R_2$ is hydrogen.

17. A compound in accordance with claim 9 wherein $R_2$ is alkyl.

18. A compound in accordance with claim 9 wherein $R_2$ is phenylalkyl.

19. A compound in accordance with claim 9 wherein $A_1$ is an α-amino acid residue and $A_2$ is an α-imino acid residue.

20. A compound in accordance with claim 9 wherein $A_2$ is L-proline.

21. A pharmaceutically acceptable compound having the formula

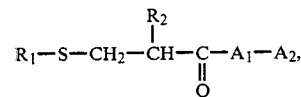

or an alkyl ester or a salt thereof, wherein
$R_1$ is hydrogen, or

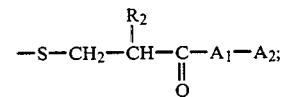

$R_2$ is hydrogen, alkyl or phenylalkyl; and
$A_1$ and $A_2$ each is an α-amino or α-imino acid residue joined through a peptide bond; said compound when administered to a mammal with elevated blood pressure being capable of reducing the blood pressure.

22. A method for reducing blood pressure in mammals which comprises administering to a mammal in need thereof, an effective amount of a compound having the formula

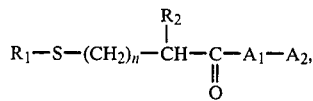

or an alkyl ester or a physiologically acceptable salt thereof, wherein $R_1$ is hydrogen, or

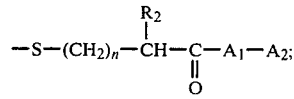

$R_2$ is hydrogen, alkyl or phenylalkyl,
n is 0 or 1; and
$A_1$ and $A_2$ each is an α-amino or, α-imino acid residue joined through a peptide bond.

* * * * *